United States Patent [19]

Badwan et al.

[11] Patent Number: 5,646,131
[45] Date of Patent: Jul. 8, 1997

[54] METHOD FOR SOLUBILIZING DRUGS USING CYCLODEXTRINS AND CARBOXYLIC ACIDS

[75] Inventors: Adnan Badwan; Abdullah Abumalooh; Muwaffak Haddadin; Hussein Ibrahim, all of Amman, Jordan

[73] Assignee: The Arab Company For Drug Industries And Medical Applicances (ACDIMA), Amman, Jordan

[21] Appl. No.: 460,631

[22] Filed: Jun. 2, 1995

Related U.S. Application Data

[63] Continuation of Ser. No. 199,523, Feb. 22, 1994, abandoned.
[51] Int. Cl.$^6$ .................. A61K 31/715; A61K 31/54; A61K 31/445; A61K 31/19
[52] U.S. Cl. .................. 514/58; 514/224.3; 514/317; 514/327; 514/568; 536/103
[58] Field of Search .................. 514/58, 224.2, 514/317, 327, 568; 536/103

[56] References Cited

U.S. PATENT DOCUMENTS

| | | | |
|---|---|---|---|
| 4,603,123 | 7/1986 | Chiesi et al. | 514/58 |
| 4,659,696 | 4/1987 | Hirai et al. | 514/15 |
| 4,727,064 | 2/1988 | Pitha | 514/58 |
| 4,891,208 | 1/1990 | Janoff et al. | 424/1 |
| 4,946,686 | 8/1990 | McClelland et al. | 424/473 |
| 5,024,998 | 6/1991 | Bodor | 514/58 |
| 5,068,226 | 11/1991 | Weinshenker et al. | 514/58 |
| 5,091,171 | 2/1992 | Yu et al. | 424/642 |

FOREIGN PATENT DOCUMENTS

| | | |
|---|---|---|
| 0274444 | 7/1988 | European Pat. Off. |
| 0346006 | 12/1988 | European Pat. Off. |
| 0413528 | 2/1991 | European Pat. Off. |
| 85/02767 | 7/1985 | WIPO |
| 94/16733 | 8/1994 | WIPO |

OTHER PUBLICATIONS

*Chemical Abstracts*, vol. 111, No. 12, abstract No. 197150p, Nov. 27, 1989.
*Patent Abstacts of Japan*, vol. 10, No. 31, C–327, Feb. 6, 1986 (abstract of JP 60–185772 published Sep. 21, 1985).
Tokumura et al., *J. Inclusion Phenomena*, vol. 2, 511–521 (1984).
Stadler–Szöke et al, *J. Inclusion Phenomena*, vol. 3, 71–84 (1985).
Szente et al, *Proc. 1st World Meeting APGI/APV*, Budapest, Hungary, May 9–11, 1995, pp. 579–580.
Duchêne, *Cyclodextrins and their Industrial uses*, Editions de Santé, Paris, 1987, Chapter 6 (211–257), Chapter 8 (297–350), Chapter 10 (393–439).
Duchêne et al, *Acta Pharma. Technol.* 36(1)6, 1–6, 1990.
Duchêne, et al, *Drug Dev. Ind. Pharm.*, 16(17), 2487–2499, 1990.
Chow et al, *Int. J. Pharm.*, 28, 95–101, 1986.
Menard et al, *Drug Dev. Ind. Pharm.*, 14(11), 1529–1547, 1988.
Otero–Espinar et al, *Int. J. Pharm.*, 75, 37–44, 1991.
Connors et al, *J. Pharm. Sci.*, 65(3), 379–383, 1976.
Uekama et al, *Chem. Pharm. Bull.*, 26(4), 1195–1200, 1978.
Zecchi et al, *Proc. Eur. Congr. Biopharm. Pharmacokinet.* 3rd, (1), 526–531, 1987.
Zecchi et al, *Pharma Acta Helv.*, 63(11), 299–302, 1988.
Orienti et al, *Arch Pharm.* (Weinheim, Germany) 322(4), 207–211, 1989.
Otero–Espinar et al, *Int. J. Pharm.*, 79, 149–157, 1992.
çelebi et al, *Int. J. Pharm.*, 78, 183–187, 1992.
Erden, *Int. J. Pharm.*, 48, 83–89, 1988.
Hassan et al, *Int. J. Pharm.*, 58, 19–24, 1990.
Menard et al, *Drug Dev. Ind. Pharm.*, 16(1), 91–113, 1990.
Kedzierewicz et al, *Int. J. Pharm.*, 58, 221–227, 1990.

*Primary Examiner*—Gary L. Kunz
*Assistant Examiner*—Kathleen Kahler Fonda
*Attorney, Agent, or Firm*—Burns, Doane, Swecker & Mathis, L.L.P.

[57] ABSTRACT

A method for enhancing the solubilization and/or complexation of a drug which is insoluble or sparingly soluble in water with cyclodextrin, comprising combining the drug with cyclodextrin together with a selected hydroxycarboxylic or polycarboxylic acid.

43 Claims, 1 Drawing Sheet

METHOD FOR SOLUBILIZING DRUGS USING CYCLODEXTRINS AND CARBOXYLIC ACIDS

This application is a continuation of application Ser. No. 08/199,523, filed Feb. 22, 1994, now abandoned.

FIELD OF THE INVENTION

This invention relates to a method for increasing the aqueous solubility and/or complexation of drugs which are insoluble or sparingly soluble in water, using cyclodextrins together with selected hydroxy-carboxylic or polycarboxylic acids.

BACKGROUND OF THE INVENTION

Cyclodextrins are cyclic multicyclopyranose units connected by $\alpha$-(1,4) linkages. The most widely known cyclodextrins are $\alpha$, $\beta$ and $\gamma$-cyclodextrins. Derivatives of these cyclodextrins with improved properties are also known and used in the pharmaceutical field. The cyclic nature of the cyclodextrins, the hydrophobic properties of their cavities as well as the hydrophilic character of their outer surfaces, enables them to interact with other chemicals and to produce inclusion compounds which are characterized by improved solubilities and stabilities. Fields of potential applications of cyclodextrins include pharmaceuticals, fine chemicals, industrial chemicals and biological active substances.

Numerous reviews and patents related to the use of cyclodextrins and their derivatives to prepare inclusion complexes of drugs are found in the literature, for example, D. Duchêne, *Cyclodextrins and their Industrial uses*, Editions de Santé, Paris, 1987, Chapter 6 (211–257), Chapter 8 (297–350), Chapter 10 (393–439); D. Duchêne et al, *Acta Pharma Technol.* 36(1)6, 1–6, 1990; D. Duchêne et al, *Drug Dev. Ind. Pharm.*, 16(17), 2487–2499, 1990; C. Hunter et al, European Patent Publication No. EP 0346006, December 1988.

Inclusion complexes prepared to specifically improve water solubility and hence bioavailability of poorly soluble drugs have been reported by workers such as D. D. Chow et al, *Int. J. Pharm.*, 28, 95–101, 1986; F. A. Menard et al, *Drug Dev. Ind. Pharm.*, 14(11), 1529–1547, 1988; F. J. Otera-Espinar et al, *Int. J. Pharm.*, 75, 37–44, 1991; and Berand M. Markarian et al, European Patent Publication No. EP 0274444, July 1988. Chemical modifications of cyclodextrins to prepare derivatives that further improve solubility of water insoluble drugs have been described, for example, by J. Pitha, U.S. Pat. No. 4,727,064, February 1988; N. S. Bodor, U.S. Pat. No. 5,024,998, July 1991.

In connection with the use of acids or buffers with cyclodextrins, the effects of the latter on dissociation constants of acidic organic compounds, including non-carboxylic acids, have been reported by K. Connors et al, *J. Pharm. Sci.*, 65 (3), 379–383, 1976, but these workers have not addressed the issue of solubility. As an extension to this work, equilibrium constants of some prostaglandins in the presence of $\alpha$- and $\beta$-cyclodextrins have been determined in phosphate buffer solutions, as reported by K. Uekama et al, *Chem. Pharm. Bull.*, 26 (4), 1195–1200, 1978. Furthermore, $\beta$-cyclodextrin inclusion complexes of several non-steroidal anti-inflammatory drugs have been correlated for their dissolution behavior at different pH values by V. Zecchi et al, Proc. *Eur. Congr. Biopharm. Pharmacokinet.* 3rd, (1), 526–531, 1987; V. Zecchi et al, *Pharma Acta Helv.*, 63 (11), 299–302, 1988; Zecchi et al concluded that the dissolution rate of such complexes is scarcely altered by changing the pH. Also, the diffusion of free and $\beta$-cyclodextrin-complexed non-steroidal anti-inflammatory drugs have been determined at different pH values by I. Orienti et al, *Arch Pharm.*(Weinheim, Germany) 322(4), 207–211, 1989. A naproxen/$\beta$-cyclodextrin complex has been examined for solubility in buffered aqueous media by F. J. Otero-Espinar et al, Int. J. *Pharm.*, 79, 149–157, 1992; N. (Celebi et al, *Int. J. Pharm.*, 78, 183–187, 1992; N. Erden, *Int. J. Pharm.*, 48, 83–89, 1988. Dissolution of famotidine, and the $\beta$-cyclodextrin inclusion compound of the drug have been reported at pH 7.4 by M. Hassan et al, *Int. J. Pharm.*, 58, 19–24, 1990. The effects of pH on the complexation of hydroclorothiazide, ibuprofen and diazepam with $\beta$-cyclodextrin cyclodextrin have been discussed by F. Menard et al, *Drug Dev. Ind. Pharm.*, 16(1), 91–113, 1990; these workers have found in their experiments that the relationship between solubility and concentration is the same at different pH levels. The dissolution of tolbutamide/$\beta$-cyclodextrin complex has been compared to that of the drug itself and solid dispersions at pH 2 by F. Kedzierewicz et al, *Int. J. Pharm.*, 58, 221–227, 1990.

Pharmaceutical formulations containing cyclodextrins typically contain other ingredients commonly used in pharmaceuticals, for example, pH adjusters (acids, bases, buffers), effervescing agents and the like, to create forms suitable for administration. For example, International Publication No. WO85/02767, July 1985, has disclosed preparing pharmaceutical compositions by dissolving a selected cyclodextrin derivative in water and adding the desired drug to form an inclusion compound, wherein the water "may further comprise physiologically compatible compounds such as sodium chloride, potassium nitrate, glycose, mannitole, sorbitol, xylitol or buffers such as phosphate, acetate or citrate buffer." Hirai et al, U.S. Pat. No. 4,659,696, April 1987, have described various non-oral, non-injectable pharmaceutical compositions containing a drug which is poorly absorbable through the gastrointestinal tract and cyclodextrin, which may contain a variety of excipients and pH adjusters, such as an acid, a base or a buffer solution. As examples of the acid, there are mentioned "inorganic acids (e.g., hydrochloric acid, boric acid, phosphoric acid, carbonic acid, bicarbonic acid, etc.), amino acids and organic acids (e.g., monocarboxylic acids, oxycarboxylic acids, polycarboxylic acids)." Also, Chiesi et al, in U.S. Pat. No. 4,603,123, July 1986, in describing pharmaceutical compositions containing piroxicam/cyclodextrin complexes, show an effervescent tablet formulation comprising citric acid and glycine sodium carbonate in equal amounts, but these are indeed typical effervescing agents and, moreover, are added after the drug/cyclodextrin complex has already been formed. Similarly, in C. Hunter, European Patent Publication No. 0346006 relating to pharmaceutical compositions comprising ibuprofen-cyclodextrin complexes, there are examples of non-effervescent, effervescent and slightly effervescent formulations comprising trisodium citrate, citric acid and sodium bicarbonate, but these ingredients are added to the already formed ibuprofen complexes. None of these earlier workers has attached any significance to particular acids, or has recognized that selected acids could be used to improve the solubilization and/or complexation with cyclodextrins of drugs which are insoluble or sparingly soluble in water. And, of course, no such improvement would be present, for example, in the case of Chiesi et al's effervescent tablets, since the citric acid component is only present in sufficient amount to effervesce together with the glycine sodium carbonate; there is no additional citric acid present to serve as a solubilizer, as provided by the present invention as described in detail hereinbelow.

Despite the advances in the pharmaceutical arts made possible by the use of cyclodextrins with drugs which are insoluble or only sparingly soluble in water, there remains a need for further improvements in drug/cyclodextrin formulations. β-Cyclodextrin, although considerably less expensive than its derivatives, increases drug solubility much more modestly than the derivatives and, in some instances, does not confer sufficient solubility at a low enough concentration to provide a feasible product, for example, a small enough tablet to be readily swallowed. Thus, there is a real need in this art for a means of significantly increasing the solubility of drugs in the less efficient cyclodextrins. On the other hand, the derivatized cyclodextrins tend to be very expensive; thus, there is also a real need for enhancing the solubility of drugs with such expensive cyclodextrins so that considerably smaller amounts of the cyclodextrins are required to achieve an effect comparable to that which could previously be obtained.

SUMMARY AND OBJECTS OF THE INVENTION

One object of the present invention is to provide a method for enhancing the solubilizing effects of cyclodextrins on drugs which are insoluble or sparingly soluble in water.

Another object of the present invention is to provide a method for enhancing the complexation of cyclodextrins with drugs which are insoluble or sparingly soluble in water.

Yet another object of the present invention is to provide a means for alleviating drug absorption problems related to the poor solubility of active agents.

Another object of the invention is to provide solid pharmaceutical formulations which are characterized by rapid dissolution and better absorption.

Another object of the invention is to provide non-alcoholic syrups and fast-dissolving tablets, capsules, effervescent tablets and/or sachets.

Still a further object of the invention is to provide effervescent tablets and/or sachets which readily dissolve in situ to solutions, thus providing a means for alleviating swallowing problems, especially in geriatric and pediatric patients.

In accord with these and other objects, the present invention provides a method for enhancing the solubilization and/or complexation of a drug which is insoluble or sparingly soluble in water with cyclodextrin, said method comprising combining said drug with cyclodextrin and an effective solubility-enhancing amount of a saturated or unsaturated $C_2$–$C_6$ carboxylic acid having from one to three —COOH groups and optionally bearing up to four —OH substituents (i.e., bearing from zero to four —OH substituents), provided that when the acid has only one —COOH group, then said acid must bear at least one —OH substituent, or a pharmaceutically acceptable salt of said acid, the weight ratio of cyclodextrin to carboxylic acid being from about 1:100 to about 100:1.

BRIEF DESCRIPTION OF THE DRAWING

Other objects and advantages of the present invention will be apparent from the following detailed description and accompanying drawing, in which the FIGURE is a series of regular cartesian plots depicting the dissolution profile of terfenadine from capsules containing the following: Δ60 mg terrenadine, 11 mg β-cyclodextrin and 30 mg citric acid; ○60 mg terfenadine, 0% β-cyclodextrin, 0% citric acid; * 60 mg terfenadine, 11 mg β-cyclodextrin, 0% citric acid; □60 mg terfenadine, 30 mg β-cyclodextrin plus 0% citric acid.

DETAILED DESCRIPTION OF THE INVENTION AND THE PREFERRED EMBODIMENTS

Figure 1:
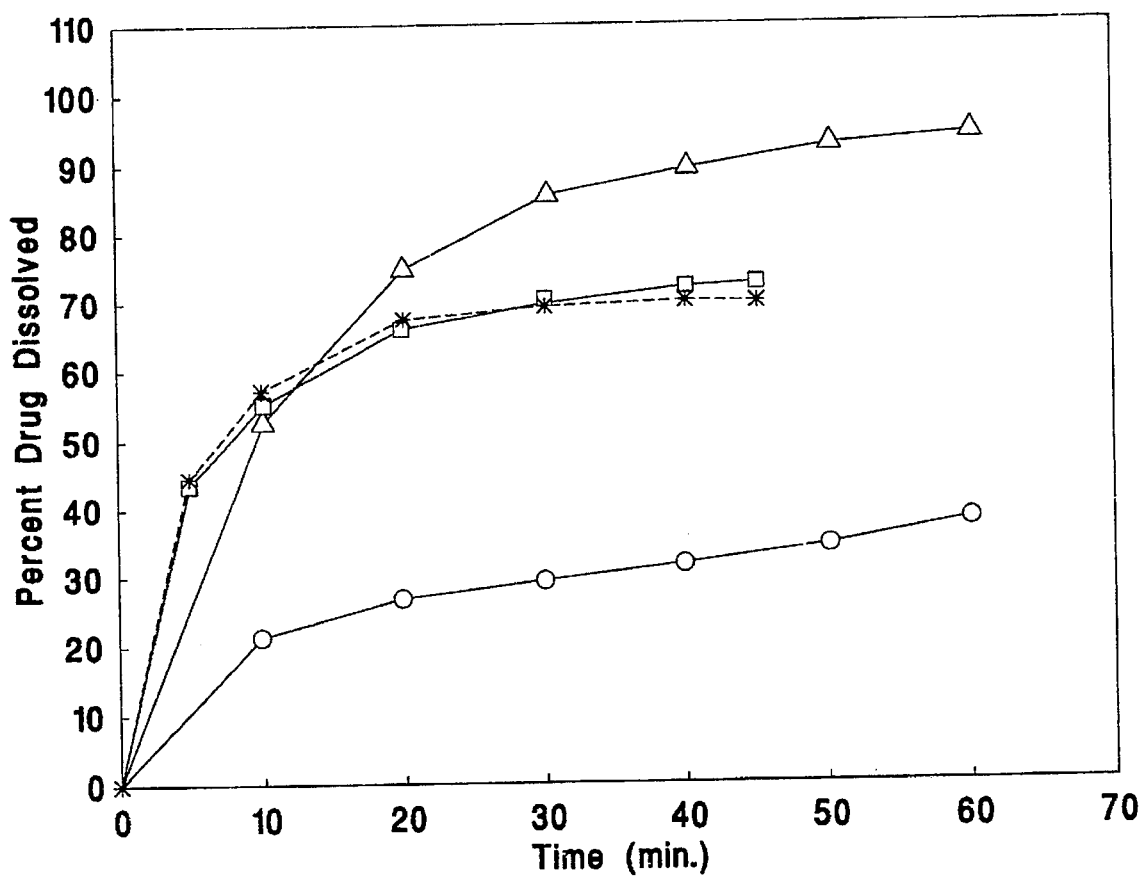

Here and throughout this description, the following definitions are applicable:

Cyclodextrins for use in the present invention include the natural cyclodextrins and their pharmaceutically acceptable derivatives. Cyclodextrins and their derivatives which have been previously described as useful for complexation with/solubilization of drugs are of particular interest herein. In addition to α-, β- and γ-cyclodextrin, derivatives of these cyclodextfins such as hydroxyalkyl (e.g., hydroxypropyl), carboxamide, diethylaminoethyl, carboxymethyl and dihydroxyalkyl (e.g., dihydroxypropyl) are of special interest, and these can be prepared by well-known procedures. For a discussion of such suitable cyclodextrin derivatives, see, for example, D. Duchêne et al, *Drug Dev. Ind. Pharm.*, 16(17), 2487–2499, 1990. Presently preferred cyclodextrins for use herein are the natural cyclodextrins, α-, β- and γ-, especially/β-cyclodextrin.

Suitable $C_2$–$C_6$ carboxylic acids for use herein can be straight- or branched-chain alkyl or alkenyl, or can even have a cyclic lactone structure. These acids are polyfunctional, i.e., multifunctional, that is, they have at least two carboxyl functions or at least one carboxyl function and at least one hydroxyl function. Such acids are thus also referred to herein as hydroxy-carboxylic acids or polycarboxylic acids, or simply as polyfunctional carboxylic acids. Appropriate acids include citric acid, tartaric acid, glutaric acid, lactic acid, ascorbic acid, glycolic acid, mevalonic acid, malic acid, tartronic acid, maleic acid, fumaric acid, malonic acid and succinic acid. Presently preferred carboxylic acids for use herein include citric acid, glutaric acid, lactic acid and tartaric acid. An especially preferred acid is citric acid. The acids can be optionally used in whole or in part in the form of their pharmaceutically acceptable salts, particularly their alkali metal salts, such as, for example, trisodium citrate.

Among the drugs which are insoluble or sparingly soluble in water and which are contemplated for use in the present invention, any of those which have been previously complexed with/solubilized by cyclodextrin are of particular interest. Of special interest herein are: non-steroidal anti-inflammatory agents, such as ibuprofen, ketoprofen, piroxicam, tenoxicam, ketorolac and naproxen; antihistaminics or antiallergics, for example, terfenadine and cinnarizine; vasodilators, oxytocic agents and abortifacients, such as prostaglandin $E_1$, prostaglandin $E_2$ and prostaglandin $F_2$; and sedatives, tranquilizers, hypnotics, anticonvulsants, anxiolytics, muscle relaxants and antispasmodics, for example, phenobarbital, pentobarbital, secobarbital, butabarbital, butalbital, sulpiride, phenytoin, diazepam, oxazepam, etomidate, bromazepam, clobazam, nitrazepam, fludiazepam, orazepam, medazepam, dimethyl diazepam, flunitrazepam, nimetazepam, pentazocine, methaqualone, salbutamol, carbamazepine, baclofen, chlorpromazine and chlordiazepoxide. Especially advantageous for enhancement of solubilization and/or complexation in accord with the present invention are basic drugs which are insoluble or sparingly soluble in water.

It is now well-known that drugs which are insoluble or sparingly soluble in water and which have the required shape and size to fit at least partially into the cavity of the hydrated cyclodextrin molecule will complex with cyclodextrin and that the drug/cyclodextrin inclusion complex which results has improved water solubility as compared to the drug itself; see, for example, International Publication No. WO85/02767, July 1985. Drugs whose water solubility can be improved by complexation with cyclodextrins exhibit significantly increased complexation and water solubility when treated in accord with the present invention. The polyfunctional carboxylic acids utilized herein make it possible to reduce the amount of cyclodextrin present in the pharmaceutical formulation, which can in turn result in substantial cost savings. Reducing the amount of cyclodextrin can also provide solid dosage forms of more reasonable size for swallowing than heretofore possible, and can result in lower toxicity. Alternatively, rather than reducing the amount of cyclodextrin present, one can instead prepare a formulation which has substantially enhanced solubility and absorption. Obviously, formulations can be made which would share these benefits, i.e., that contain somewhat less cyclodextrin while still exhibiting improved drug solubility and absorption. Preferred pharmaceutical formulations provided by the present invention include non-alcoholic syrups and rapidly dissolving tablets, capsules, effervescent tablets and/or sachets. The latter two solid preparations can be converted in situ to solutions, thus providing a means for alleviating swallowing problems in geriatric and pediatric patients.

In accord with the present invention, it has now been discovered that use of a hydroxy-carboxylic or polycarboxylic acid and/or a salt thereof as defined hereinabove together with α, β or γ-cyclodextrin or a pharmaceutically acceptable derivative thereof results in a dramatic increase in the solubility of drugs which are insoluble or sparingly soluble in water, enhancing the solubilizing and/or complexing ability of the cyclodextrins for the drug through the presence of the selected polyfunctional acid component. Advantageously, the acid, cyclodextrin and drug can be combined with each other in the process of preparing the pharmaceutical composition/formulation, so that the complexing/solubilizing takes place in the course of preparing the final dosage form and need not be carried out separately beforehand. Indeed, in the case of effervescent tablets, sachets and the like, the actual complexation/solubilization will typically occur when the tablet or similar solid dosage form is dissolved in water shortly before administration to the patient.

As noted hereinabove, in preparing the formulations of the invention, the weight ratio of cyclodextrin to selected carboxylic acid and/or salt of said acid is from about 1:100 to about 100: 1. More preferably, the weight ratio of cyclodextrin to acid ingredient is from about 1:50 to 50: 1,most preferably from about 1:5 to about 5:1.

Typical compositions prepared in accord with the present invention comprise the selected cyclodextrin at a weight percent of from about 0.05 to about 8% of the total weight and the selected hydroxy-carboxylic or polycarboxylic acid and/or salt thereof at a concentration ranging from about 0.1 to about 5% total weight. However, in selected solid dosage forms, considerably greater amounts of cyclodextrin and polyfunctional acid are typically used, for example from about 15 to about 30% by weight of cyclodextrin and from about 5 to 10% by weight of the acid as solubilization enhancer. Greater amounts of the acid/salt can be present in such formulations if that ingredient is serving another purpose in the composition, for example, as an effervescing agent.

In preferred embodiments, the present invention provides non-alcoholic aqueous syrups of water-insoluble or sparingly insoluble drugs, which syrups are advantageous over suspensions and/or hydroalcoholic solutions of such drugs; and rapidly dissolving solid dosage forms which can be quickly and conveniently converted in situ to aqueous solutions which can be readily administered to patients who have difficulty in swallowing, such as pediatric and geriatric patients. The pharmaceutical preparations prepared in accord with this invention are stable and non-irritating, have very low systemic or local toxicity and are generally well-suited for oral and parenteral administration, depending of course upon the properties of the selected ingredients, particularly the cyclodextrin and the drug. Formulations for oral use can be enhanced by the addition of a taste-masking agent, flavoring agent and/or sweetener. Other ingredients commonly used in oral dosage forms can also be present. In the case of parenteral formulations, the ingredients will be in an aqueous solution suitable for injection, i.e., sterile and pyrogen free and prepared in accord with accepted pharmaceutical procedure. Again, other ingredients typically used in such formulations can be present.

While not wishing to be bound by any particular theory of operation, applicants believe that the acids which are selected for use herein form aggregates by virtue of the fact that they possess both polar and non-polar groups, that these aggregates combine with the selected cyclodextrin to enhance solubilization/complexation of the drug, and that the selected acid needs to be present in sufficient quantity to form aggregates in order for enhancement of solubility to occur. Thus it appears that the acid participates directly in the drug complex formation, acting as a co-complexing agent with the cyclodextrin and resulting in a new three-way co-complex of drug, cyclodextrin and acid.

Pharmaceutical compositions prepared in accord with the present invention can be used to treat a variety of conditions, depending upon the pharmacological nature of the drug selected for administration. The compositions comprise a pharmacologically/therapeutically effective amount of the selected drug and the amount/ratios of selected cyclodextrin and selected polyfunctional acid or salt thereof described hereinabove. For example, if the selected drug is an antihistaminic or antiallergic, for example, terfenadine, a pharmacologically effective amount thereof will be an amount sufficient to provoke an antihistaminic or antiallergic response (e.g., in the treatment of symptoms associated with seasonal allergic rhinitis, such as sneezing, lacrimation, pruritus and rhinorrhea). As a further example, when the selected drug is an anti-inflammatory agent, for example ketoprofen, a pharmacologically effective amount thereof will be an amount sufficient to elicit an anti-inflammatory response (such as in the treatment of rheumatoid arthritis or osteoarthritis), or an amount sufficient to elicit an analgesic effect (since ketoprofen and other non-steroidal anti-inflammatory agents are frequently used for their analgesic as well as their anti-inflammatory properties). In short, the instant compositions are typically used for those purposes for which the drug component of the composition is itself known to be useful.

Generally speaking, the therapeutic dosage ranges for administration of drugs in the pharmaceutical compositions/formulations described herein will be the same as or less than those characteristically used for administration of the drug per se. Naturally, such therapeutic dosage ranges will vary with the size and species of the patient, the condition for which the formulation is administered, the route of administration employed and the like. The quantity of given dosage form needed to deliver the desired dose of active ingredients will of course depend upon the concentration of the drug in the pharmaceutical formulation.

In order to further illustrate the present invention and the advantages thereof, the following specific examples are given, it being understood that some are intended only as illustrative and in no way limitative of the invention.

The terfenadine stability testing referred to in Examples 2 and 4 hereinbelow was based on the assay method described in a terfenadine monograph by A. Badwan et al appearing in *Analytical Profiles of Drug Substances*, volume 19, ed. K. Florey, Academic Press, Inc., San Diego, Calif., 1990, pp. 627–662. The actual assay method was as follows:

A quantity of the mixed contents of 20 capsules containing the equivalent of 60 mg terfenadine was transferred to a 100 ml volumetric flask. 70 ml of methanol were added and the mixture was shaken for 20 minutes, then methanol was added to volume, and the contents of the flask were mixed and centrifuged. The first derivative ultraviolet absorption spectra of the solutions (1) and (2) using methanol as the blank and a path length of 1 cm in the range of 300–200 nm at a speed of 120 nm/min and λ=2.0 were recorded. Solution (1) was the sample solution prepared. Solution (2) was a standard solution of terfenadine in the same medium having a known concentration of about 600 /µg/ml. The amplitude obtained at about 270 nm was measured for sample and standard solutions. The quantity, in mg of ($C_{32}H_{41}NO_2$), in the portion of capsules content was calculated according to the formula:

$$\frac{D_s}{D_{st}} \times 100 \, C$$

wherein C is the concentration, in µg per ml, of terfenadine in the standard solution, and $D_s$ and $D_{st}$ are the first derivative amplitude of the solution of sample and standard, respectively.

EXAMPLE 1

Working models showing the effectiveness of the invention in increasing the solubility of representative water-insoluble or sparingly soluble drugs are shown in TABLE I below. The solubilities (in mg/ml) of the drugs were investigated at 30° C., in water; in water containing 2% β-cyclodextrin; and in aqueous solution of 2% selected cyclodextrin and 1% selected polyfunctional acid or corresponding salt.

EXAMPLE 2

Preparation of Syrups

Syrups prepared in accord with the present invention typically contain water-insoluble or sparingly soluble drugs in an amount of from about 6 to about 600 mg/ml of syrup. The syrups generally contain the solubilizing agent, i.e., α,β, γ cyclodextrin or derivative thereof, in an amount of from about 0.1 to about 5% of the syrup and the solubilization augmenting agent, i.e., the hydroxy-carboxylic acid or polycarboxylic acid, in an amount of from about 0.1 to about 5% of the syrup. The syrups are preferably buffered to control the pH value to about pH 3 to 7, more preferably pH 3.5 to 5. The preferred buffering system is a combination of the selected acid and its corresponding salt in an amount of from about 0.1 to about 5% for the acid and a similar range for the corresponding salt. The syrups typically contain sufficient viscosity imparting agents (such as polyvinylpyrrolidone) in an amount of from about 1 to about 3% of the syrup and medium-building agents such as glycerine, propylene glycol or sorbitol in an amount of from about 10 to about 35% of the syrup. These additives are included to render the medium more viscous, thus preventing the solution from spilling over when administered by a spoon or the like. To mask the undesirable taste of the drug, the syrups generally contain sufficient sweetening agents such as sucrose in an amount of from about 20 to about 30% of the syrup. Other sweetening agents such as saccharin sodium could be used in an amount of from about 0.1 to about 0.2% of the syrup.

Additional ingredients such as coloring or flavoring agents can be incorporated to enhance the quality of the syrup, if desired. Water is present as the main vehicular agent in the syrups and is added to the desired volume.

In any event the weight ratio of cyclodextrin to acid in syrup formulations is as broadly described hereinabove, but preferably is from about 1:5 to 5:1, and more preferably from about 3:1 to about 1:1.

TABLE I

Solubilities (mg/ml) of Drugs in Water, in Water Containing 2% β-Cyclodextrin (CD), and in Aqueous Solution of 2% Cyclodextrin, 1% Hydroxy-Carboxylic or Polycarboxylic Acid or Corresponding Salt, at 30° C.

| DRUG | Water | 2% aq. BETA CD soln. | BETA-CYCLODEXTRIN + | | | ALPHA-CYCLODEXTRIN, + | | | GAMMA-CYCLODEXTRIN + | | | |
|---|---|---|---|---|---|---|---|---|---|---|---|---|
| | | | Citric acid | Glutaric acid | Lactic acid | Tartaric acid | Citric acid | Glutaric acid | Lactic acid | Tartaric acid | Citric acid | Glutaric acid | Lactic acid | Tartaric acid |

| DRUG | Water | 2% aq. BETA CD soln. | Citric acid | Glu-taric acid | Lactic acid | Tar-taric acid | Citric acid | Glu-taric acid | Lactic acid | Tar-taric acid | Citric acid | Glutaric acid | Lactic acid | Tartaric acid |
|---|---|---|---|---|---|---|---|---|---|---|---|---|---|---|
| Terfenadine | <0.01 | 0.01 | 5.68 | 5.49 | 8.87 | 5.21 | 2.15 | 7.17 | 6.27 | 1.31 | 2.20 | 6.08 | 7.34 | 1.22 |
| Ibuprofen | <0.01 | 0.69 | 2.95* | 3.00* | 1.65* | 1.36* | | | | | | | | |
| Cisapride | 0.003 | 0.015 | 0.55 | 2.07 | 11.4 | 4.38 | | | | | | | | |
| Ketoprofen | 0.005 | 1.64 | 7.06* | | | | | | | | | | | |
| Piroxicam | insoluble | 0.072 | 0.78* | | | | | | | | | | | |

(*) Solubility in aqueous solution containing 2% β-cylcodextrin and 1% trisodium salt.

| Part A: Terfenadine Syrup (6 mg/ml) | |
|---|---|
| Ingredient | Concentration (mg/ml) |
| Terfenadine | 6 |
| Propylene glycol | 250 |
| Glycerin | 100 |
| Sucrose | 300 |
| Citric acid, 1 H$_2$O (monohydrated) | 10 |
| Trisodium citrate, 2 H$_2$O (dihydrated) | 10 |
| β-Cyclodextrin | 30 |
| Sodium saccharin | 1 |
| Polyvinylpyrrolidine (K30) | 20 |
| Water | q.s. |

Method of Preparation for 100 ml of Syrup
1. Dissolve citric acid and trisodium citrate in 10 ml of deionized water.
2. Dissolve sucrose and β-cyclodextrin in 10 ml of deionized water.
3. Dissolve polyvinylpyrrolidone and sodium saccharin in 10 ml of deionized water.
4. Mix terfenadine, propylene glycol and glycerin, then, while stirring and heating, add the solutions prepared in steps 1–3. Continue mixing until the drug is dissolved.
5. Add water to the desired volume, then mix for 20 minutes.

A syrup made as described above was tested for stability at room temperature (RT) and at the accelerated temperatures of 55° and 65° C., with the following results.

| Storage Time (days) | 65° C. Assay (%) | pH | 55° C. Assay (%) | pH | RT Assay (%) | pH |
|---|---|---|---|---|---|---|
| 0 | 99.1 | 4.5 | 99.1 | 4.5 | 99.1 | 4.6 |
| 11 | 99.4 | 4.6 | 99.4 | 4.5 | — | — |
| 27 | 103.0 | 4.5 | 100.3 | 4.5 | — | — |
| 53 | 101.0 | — | — | — | — | — |
| 83 | — | — | — | — | 101.0 | 4.6 |
| 580 | — | — | — | — | 100.0 | 4.6 |

Other examples of syrups made in accord with the present invention are demonstrated by the ketoprofen syrup and cisapride syrup, as described below.

| Ingredient | Concentration (mg/ml) |
|---|---|
| Part B: Ketoprofen Syrup (10 mg/ml) | |
| Ketoprofen | 10 |
| Propylene glycol | 250 |
| Glycerin | 100 |
| Sucrose | 300 |
| Trisodium citrate | 15 |
| β-Cyclodextrin | 30 |
| Polyvinylpyrrolidone (K30) | 20 |
| Water | q.s. |
| Part C: Cisapride Syrup (1 mg/ml) | |
| Cisapride | 1 |
| Propylene glycol | 300 |
| Tartaric acid | 10 |
| β-Cyclodextrin | 20 |
| Sorbitol 70% | 500 |
| Sodium saccharin | 1 |
| Polyvinylpyrrolidone (K30) | 2 |
| Water | q.s. |

Syrups made in accord with the present invention have an advantage over other possible liquid formulations in being devoid of alcohol, an essential ingredient used to increase solubility of water-insoluble drugs. They offer a wider range of concentrations of the water-insoluble drugs compared to other liquid formulations. Consequently, they provide a means for better control of dose administration and greater absorption of said drugs.

EXAMPLE 3

Preparation of Effervescent Tablets

Effervescent tablets prepared in accord with the present invention typically contain water-insoluble or sparingly soluble drugs in an amount of from about 10 to about 800 mg per tablet. The tablets generally contain the solubilizing agent α, β, γ-cyclodextrin or derivative thereof in an amount of from about 15 to about 30% of the tablet and the solubilization augmenting agent, preferably citric or tartaric acid, in an amount of from about 5 to about 10% of the tablet. An additional amount of citric acid, from about 15 to about 35% of the tablet, is typically added to the formula to produce the desired effervescent action. The tablets generally contain sodium bicarbonate in an amount of from about 5 to about 30% of the tablet to react with part of the acid and produce the effervescent action. Other additives can be added to the formula to give body to the tablet and help bind the ingredients; e.g., soluble starch or Aerosil™ in an amount of from about 25 to about 125 mg of the tablet. Other additives such as ethyl alcohol or 5% Tween™80 solutions can be added, if desired, in sufficient quantities to granulate the powders. The formula can also contain other ingredients such as a sweetener or a taste-masking agent to improve taste and a soluble lubricating agent such as sodium benzoate to facilitate tablet compression. In any case, the weight ratio of cyclodextrin to acid in effervescent tablets is as broadly described hereinabove, but preferably is from about 1:5 to 5:1, and more preferably from about 1:4 to about 1:1. An illustrative formulation is shown below.

| Part A: Terfenadine Effervescent Tablets (60 mg) | |
|---|---|
| Ingredient | Amount (g) |
| Terfenadine | 0.06 |
| Sodium bicarbonate | 0.75 |
| β-Cyclodextrin | 1.25 |
| Saccharin sodium | 0.05 |
| Sucrose | 1.00 |
| Citric acid, anhydrous | 2.00 |
| Sodium benzoate | 0.15 |
| Flavoring agent | q.s. |

Method of Preparation of Effervescent Tablets
1. Mix β-cyclodextrin with sodium bicarbonate.
2. Mix powdered sugar, saccharin sodium and mixture from Step 1 with terfenadine in a suitable mixer.
3. Granulate resultant mix with ethyl alcohol.
4. Sieve and dry resulting granules.
5. Mix granules with citric acid, sodium benzoate and flavoring agent.
6. Compress into tablets.

Effervescent tablets made as described above, when tested in 100 ml of water, achieved complete dissolution, with effervescence, in 2–4 minutes. Terfenadine assayed at 95–97% of the nominal amount.

Another example of effervescent tablets prepared in accord with the present invention is demonstrated in the following example.

| Part B: Cisapride Effervescent Tablets (10 mg) | |
| --- | --- |
| Ingredient | Amount (mg) |
| Cisapride (anhydrous) | 10 |
| Citric acid, anhydrous | 65 |
| Tartaric acid | 250 |
| Sodium bicarbonate | 200 |
| Aerosil ™ (silica aerogel) | 25 |
| Sodium benzoate | 20 |
| Soluble starch | 25 |
| β-Cyclodextrin | 50 |
| Flavoring agent | q.s. |

Method of Preparation of Cisapride Effervescent Tablets
1. Mix β-cyclodextrin with sodium bicarbonate, soluble starch and cisapride.
2. Granulate the mixture with ethyl alcohol.
3. Sieve and dry the resulting granules.
4. Mix granules with citric acid, tartaric acid, sodium benzoate, the flavoring agent and Aerosil™.
5. Compress into tablets.

The effervescent tablets, when tested in 100 ml of water, dissolved with effervescence in 2–3 minutes, forming a solution containing 10 mg of the drug and of pH≃4.

Effervescent tablets made in accord with the present invention provide a means for preparing solutions of water-insoluble drugs in situ. Such solutions are readily absorbed and are well-suited for geriatric and pediatric patients.

EXAMPLE 4

Preparation of Fast-Dissolving Capsules

Rapidly dissolving capsules prepared in accordance with the present invention typically contain water-insoluble or sparingly soluble drugs in an amount of from about 6 to about 600 mg of the capsule. The capsules typically contain the solubilizing agent α, β or γ,-cyclodextrin or derivative thereof in an amount of from about 0.1 to about 5% of the capsule and the solubilization augmenting hydroxycarboxylic or polycarboxylic acid in an amount of from about 0.1 to about 5% of the capsule. The formula generally contains additives to give body to the granules, e.g., calcium hydrogen phosphate, and Avicel™ in amounts of from about 25 to about 30% and about 5 to about 10% of the capsule, respectively. Binding agents and/or wetting agents such as PEG 4000, Tween™80, sodium lauryl sulfate and PVP to granulate the powder mix are typically added to the formula in an amount of from about 0.1 to about 5% of the capsule. The formula typically contains disintegrants and swelling agents such as Primojel™, maize starch, and Aerosil™ in an amount of from about 1 to about 10%. The formula can contain other ingredients, such as a sweetener. In any event, the weight ratio of cyclodextrin to acid in rapidly dissolving capsule formulations will be as broadly described hereinabove, but preferably will be from about 1:5 to 5:1, and more preferably from about 3:1 to about 1:1. The following illustrates such a formulation.

| Terfenadine Capsule (60 mg) | |
| --- | --- |
| Ingredient | Amount (mg) |
| Terfenadine | 60 |
| Polyethylene glycol 4000 | 24 |
| Tween ™ 80 | 3 |

-continued

| Terfenadine Capsule (60 mg) | |
| --- | --- |
| Ingredient | Amount (mg) |
| Calcium hydrogen phosphate | 28 |
| Maize starch | 4 |
| Sodium lauryl sulfate | 1 |
| Avicel ™ pH 101 (microcrystalline cellulose) | 72 |
| β-cyclodextrin | 11 |
| Citric acid, anhydrous | 30 |
| Polyvinylpyrrolidone (K30) | 12 |
| Primojel ™ | 10 |
| Aerosil ™ (silica aerogel) | 8 |

Method of Preparation of Fast-Dissolving Terfenadine Capsules
1. Mix calcium hydrogen phosphate, maize starch, sodium lauryl sulfate and Avicel™ with hot alcoholic solution of terfenadine, PEG and Tween™80. Maintain mixing until powder is dry. Pass through 0.8 mm sieve.
2. Granulate with 20 ml aqueous solution containing PVP and citric acid. Pass granules through 0.8 mm sieves, then dry at 40° C.
3. Add Primojel™, Aerosil™ and cyclodextrin to granules and mix for 10 minutes.
4. Fill capsules with granules.

Capsules made as described above were tested for dissolution and chemical stability with the following results.

| Storage Time (weeks) | 65° C. Assay (%) | 44° C. Assay (%) | RT Assay (%) |
| --- | --- | --- | --- |
| 0 | 99.6 | 99.6 | 99.6 |
| 1 | 98.8 | — | — |
| 2 | 98.5 | — | — |
| 3 | 98.6 | — | — |
| 4 | 97.9 | 100.2 | — |
| 6 | 98.2 | — | — |
| 12 | — | 99.3 | 99.2 |
| 24 | — | 99.0 | 99.4 |

A comparison of the dissolution profile of terrenadine from capsules prepared as in the forgoing example (Δ) and from identical controls devoid of cyclodextrin and citric acid (○), or devoid of citric acid and containing the same (*) or greater (□) amounts of cyclodextrin, is shown in the FIGURE. As is readily apparent from the FIGURE, the control containing 11 mg of β-cyclodextrin (*) had greatly improved dissolution over the control containing no cyclodextrin (○). However, increasing the amount of cyclodextrin in the capsule from 11 mg to 30 mg of β-cyclodextrin (□) did not further improve dissolution to a significant extent. In contrast, the capsule prepared in accord with the present invention containing 11 mg of β-cyclodextrin and 30 mg of citric acid (Δ) substantially improved dissolution of terfenadine over all of the control formulations.

Capsules made in accordance with the invention ensure complete dissolution of the required dose of the water-insoluble drug within an acceptable time span. Therefore, such capsules provide a means to ensure better absorption of the drugs and hence, better bioavailability than comparable dosage forms.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A method for enhancing the solubilization of a drug which is insoluble or sparingly soluble in water with cyclodextrin, said method comprising combining in water said drug with cyclodextrin and an effective solubility-enhancing amount of saturated or unsaturated $C_2$–$C_6$ carboxylic acid having from one to three —COOH groups and bearing from zero to four —OH substituents, provided that when the acid has only one —COOH group, then said acid must bear at least one —OH substituent, or a pharmaceutically acceptable salt of said acid, the weight ratio of cyclodextrin to carboxylic acid being from about 1:50 to about 50:1.

2. The method according to claim 1, wherein the cyclodextrin comprises α-, β- or γ-cyclodextrin or a pharmaceutically acceptable derivative thereof.

3. The method according to claim 2, wherein the cyclodextrin derivative comprises a hydroxyalkyl, carboxamide, diethylaminoethyl, carboxymethyl or dihydroxyalkyl derivative of α-, β- or γ,-cyclodextrin.

4. The method according to claim 2, wherein the cyclodextrin comprises β-cyclodextrin.

5. The method according to claim 1, wherein the $C_2$–$C_6$ carboxylic acid comprises citric acid, tartaric acid, glutaric acid, lactic acid, ascorbic acid, glycolic acid, mevalonic acid, malic acid, tartronic acid, maleic acid, fumaric acid, malonic acid or succinic acid, or a pharmaceutically acceptable salt thereof.

6. The method according to claim 5, wherein the $C_2$–$C_6$ carboxylic acid or salt is citric acid, trisodium citrate, tartartic acid or a combination of citric acid and trisodium citrate.

7. The method according to claim 1, wherein the drug is a non-steroidal anti-inflammatory agent.

8. The method according to claim 7, wherein the drug is ibuprofen, ketoprofen, piroxicam, tenoxicam, ketorolac or naproxen.

9. The method according to claim 1, wherein the drug is an antihistaminic or antiallergic.

10. The method according to claim 9, wherein the drug is terfenadine or cinnarizine.

11. The method according to claim 1, wherein the drug is a vasodilator, oxytocic agent or abortifacient.

12. The method according to claim 11, wherein the drug is prostaglandin $E_1$, prostaglandin $E_2$ or prostaglandin $F_2$.

13. The method according to claim 1, wherein the drug is a sedative, tranquilizer, hypnotic, anticonvulsant, anxiolytic, muscle relaxant or antispasmodic.

14. The method according to claim 13, wherein the drug is phenobarbital, pentobarbital, secobarbital, butabarbital, butalbital, sulpiride, phenytoin, diazepam, oxazepam, etomidate, bromazepam, clobazam, nitrazepam, fludiazepam, lorazepam, medazepam, dimethyl diazepam, flunitrazepam, nimetazepam, pentazocine, methaqualone, salbutamol, carbamazepine, baclofen, chlorpromazine or chlordiazepoxide.

15. The method according to claim 1, wherein the drug is terfenadine, ketoprofen, cisapride or ibuprofen, the cyclodextrin is β-cyclodextrin and the $C_2$–$C_6$ carboxylic acid or salt is citric acid, trisodium citrate, tartaric acid or a combination of citric acid and trisodium citrate.

16. The method of claim 1 wherein the drug is terfenadine.

17. The method according to claim 16, wherein the cyclodextrin comprises α-, β- or γ-cyclodextrin or a pharmaceutically acceptable derivative thereof.

18. The method according to claim 17, wherein the cyclodextrin derivative comprises a hydroxyalkyl, carboxamide, diethylaminoethyl, carboxymethyl or dihydroxyalkyl derivative of α-, β- or γ-cyclodextrin.

19. The method according to claim 17, wherein the cyclodextrin comprises β-cyclodextrin.

20. The method according to claim 16, wherein the $C_2$–$C_6$ carboxylic acid comprises citric acid, tartaric acid, glutaric acid, lactic acid, ascorbic acid, glycolic acid, mevalonic acid, malic acid, tartronic acid, maleic acid, fumaric acid, malonic acid or succinic acid, or a pharmaceutically acceptable salt thereof.

21. The method according to claim 20, wherein the $C_2$–$C_6$ carboxylic acid or salt is citric acid, trisodium citrate, tartartic acid or a combination of citric acid and trisodium citrate.

22. The method according to claim 16, wherein the cyclodextrin is β-cyclodextrin and the $C_2$–$C_6$ carboxylic acid or salt is citric acid, trisodium citrate, tartaric acid or a combination of citric acid and trisodium citrate.

23. The method of claim 1 wherein the drug is ibuprofen.

24. The method according to claim 23, wherein the cyclodextrin comprises α-, β- or γ-cyclodextrin or a pharmaceutically acceptable derivative thereof.

25. The method according to claim 24, wherein the cyclodextrin derivative comprises a hydroxyalkyl, carboxamide, diethylaminoethyl, carboxymethyl or dihydroxyalkyl derivative of α-, β- or γ-cyclodextrin.

26. The method according to claim 24, wherein the cyclodextrin comprises β-cyclodextrin.

27. The method according to claim 23, wherein the $C_2$–$C_6$ carboxylic acid, comprises citric acid, tartaric acid, glutaric acid, lactic acid, ascorbic acid, glycolic acid, mevalonic acid, malic acid, tartronic acid, maleic acid, fumeric acid, malonic acid or succinic acid, or a pharmaceutically acceptable salt thereof.

28. The method according to claim 27, wherein the $C_2$–$C_6$ carboxylic acid or salt is citric acid, trisodium citrate, tartartic acid or a combination of citric acid and trisodium citrate.

29. The method according to claim 23, wherein the cyclodextrin is β-cyclodextrin and the $C_2$–$C_6$ carboxylic acid or salt is citric acid, trisodium citrate, tartaric acid or a combination of citric acid and trisodium citrate.

30. The method of claim 1 wherein the drug is cisapride.

31. The method according to claim 30, wherein the cyclodextrin comprises α- β- or γ-cyclodextrin or a pharmaceutically acceptable derivative thereof.

32. The method according to claim 31, wherein the cyclodextrin derivative comprises a hydroxyalkyl, carboxamide, diethylaminoethyl, carboxymethyl or dihydroxyalkyl derivative of α-or β- or γ-cyclodextrin.

33. The method according to claim 31, wherein the cyclodextrin comprises β-cyclodextrin.

34. The method according to claim 30, wherein the $C_1$–$C_6$ carboxylic acid comprises citric acid, tartaric acid, glutaric acid, lactic acid, ascorbic acid, glycolic acid, mevalonic acid, malic acid, tartonic acid, maleic acid, fumaric acid, malonic acid or succinic acid, or a pharmaceutically acceptable salt thereof.

35. The method according to claim 34, wherein the $C_2$–$C_6$ carboxylic acid or salt is citric acid, trisodium citrate, tartaric acid or a combination of citric acid and trisodium citrate.

36. The method according to claim 30, wherein the cyclodextrin is β-cyclodextrin and the $C_2$–$C_6$ carboxylic acid or salt is citric acid, trisodium citrate, tartaric acid or a combination of citric acid and trisodium citrate.

37. The method of claim 1 wherein the drug is piroxicam.

38. The method according to claim 37, wherein the cyclodextrin comprises α-, β- or γ-cyclodextrin or a pharmaceutically acceptable derivative thereof.

39. The method according to claim 38, wherein the cyclodextrin derivative comprises a hydroxyalkyl, carboxamide, diethylaminoethyl, carboxymethyl or dihydroxyalkyl derivative of α-, β- or γ-cyclodextrin.

40. The method according to claim 38, wherein the cyclodextrin comprises β-cyclodextrin.

41. The method according to claim 37, wherein the $C_2$–$C_6$ carboxylic acid comprises citric acid, tartaric acid, glutaric acid, lactic acid, ascorbic acid, glycolic acid, mevalonic acid, malic acid, tartronic acid, maleic acid, fumaric acid, malonic acid or succinic acid, or a pharmaceutically acceptable salt thereof.

42. The method according to claim 41, wherein the $C_2$–$C_6$ carboxylic acid or salt is citric acid, trisodium citrate, tartaric acid or a combination of citric acid and trisodium citrate.

43. The method according to claim 37, wherein the cyclodextrin is β-cyclodextrin and the $C_2$–$C_6$ carboxylic acid or salt is trisodium citrate.

* * * * *